US012564624B2

(12) United States Patent
Tsukamoto

(10) Patent No.: US 12,564,624 B2
(45) Date of Patent: Mar. 3, 2026

(54) OSTRICH ANTIBODY FOR BACTERIAL INFECTIOUS DISEASES

(71) Applicant: OSTRICH PHARMA KK, Kyoto (JP)

(72) Inventor: Yasuhiro Tsukamoto, Osaka (JP)

(73) Assignee: OSTRICH PHARMA KK, Kyoto (JP)

( * ) Notice: Subject to any disclaimer, the term of this patent is extended or adjusted under 35 U.S.C. 154(b) by 0 days.

(21) Appl. No.: 18/632,343

(22) Filed: Apr. 11, 2024

(65) Prior Publication Data

US 2024/0335519 A1     Oct. 10, 2024

Related U.S. Application Data

(62) Division of application No. 16/760,432, filed as application No. PCT/JP2018/040729 on Nov. 1, 2018, now abandoned.

(30) Foreign Application Priority Data

Nov. 2, 2017     (WO) .................. PCT/JP2017/039828

(51) Int. Cl.
| | |
|---|---|
| *A61K 39/08* | (2006.01) |
| *A23G 3/36* | (2006.01) |
| *A61K 39/00* | (2006.01) |
| *A61K 39/02* | (2006.01) |
| *A61K 39/085* | (2006.01) |
| *A61K 39/395* | (2006.01) |
| *A61P 31/04* | (2006.01) |

(52) U.S. Cl.
CPC .............. *A61K 39/08* (2013.01); *A23G 3/366* (2013.01); *A61K 39/085* (2013.01); *A61K 39/107* (2013.01); *A61K 39/395* (2013.01); *A61P 31/04* (2018.01); *A61K 2039/505* (2013.01)

(58) Field of Classification Search
CPC .................. A61K 39/08; A61K 39/395; A61K 2039/505; A23G 3/364; A23G 3/66; A61P 31/04; C07K 16/1282; C07K 16/1239; C07K 16/1278; C07K 2317/11; C07K 2317/23; C07K 2317/76; C07K 2317/94; A23L 33/135; Y02A 50/30
See application file for complete search history.

(56) References Cited

U.S. PATENT DOCUMENTS

| | | | | |
|---|---|---|---|---|
| 5,601,823 A | * | 2/1997 | Williams | ............... C07K 16/02 424/157.1 |
| 2014/0234337 A1 | * | 8/2014 | Tsukamoto | ............. A61P 37/08 530/389.4 |
| 2016/0304623 A1 | | 10/2016 | Tsukamoto | |

FOREIGN PATENT DOCUMENTS

| | | |
|---|---|---|
| CN | 103533958 A | 1/2014 |
| CN | 103890173 A | 6/2014 |

(Continued)

OTHER PUBLICATIONS

International Search Report for related International Application No. PCT/JP2018/040729 mailed Jan. 8, 2019.

(Continued)

*Primary Examiner* — Jana A Hines
(74) *Attorney, Agent, or Firm* — Renner, Otto, Boisselle & Sklar, LLP

(57) ABSTRACT

A method of manufacturing ostrich antibodies may include immunizing mature female ostriches with a mixture solution comprising *Clostridium difficile* toxin A and toxin B, obtaining eggs from the immunized ostriches, and purifying egg yolk antibodies from the eggs.

9 Claims, 9 Drawing Sheets

C. difficile Toxin A concentration

(56) References Cited

FOREIGN PATENT DOCUMENTS

| | | | | | |
|----|---------------|---|---------|-----|------------|
| JP | 2003503015 A | | 1/2003 | | |
| JP | 2008-169142 A | | 7/2008 | | |
| JP | 2013-505289 A | | 2/2013 | | |
| JP | 2007145808 | * | 4/2013 | ........... | A61K 39/395 |
| JP | 2015505815 A | | 2/2015 | | |
| JP | 2016-88873 A | | 5/2016 | | |
| JP | 2016-88937 A | | 5/2016 | | |
| JP | 2017-6008 A | | 1/2017 | | |
| JP | 2017-184669 A | | 10/2017 | | |
| WO | 0071585 A1 | | 11/2000 | | |
| WO | 2011/036539 A1 | | 3/2011 | | |
| WO | 2012071346 A1 | | 5/2012 | | |
| WO | 2013/027356 A1 | | 2/2013 | | |
| WO | 2013066876 A1 | | 5/2013 | | |
| WO | WO-2014169344 A1 | * | 10/2014 | ............ | A61K 39/40 |
| WO | 2015083374 A1 | | 6/2015 | | |

OTHER PUBLICATIONS

Tobias, F.L. et al., "Growth inhibition of *Staphylococcus aureus* and *Escherichia coli* strains by neutralizing IgY antibodies from ostrich egg yolk", Brazilian Journal of Microbiology, Apr. 2012, vol. 43, No. 2, pp. 544-551.

Shi, Huaying et al., "Effects of specific egg yolk immunoglobulin on pan-drug-resistant Acinetobacter baumannii", Biomedicine & Pharmacotherapy [online], Oct. 6, 2017, [retrieval date Dec. 11, 2018] vol. 95, pp. 1734-1742.

Topiiescu, Georgiana et al., "Growth Inhibition of antibiotic resistant bacteria by neutralizing IgY antibodies", Journal of Biotechnology [online], Sep. 3, 2014, [retrieval date Dec. 11, 2018], vol. 185, supplement, pp. S91-S92.

Ostrigen Inc., "Ostrich antibody candy is made, curing diarrhea that is one among two leading causes of death in children", Ready for [online], Aug. 31, 2015, [retrieval date Dec. 11, 2018] and partial English translation.

International Search Report for related International Application No. PCT/JP2017/039828 mailed Jan. 30, 2018.

Official Action for corresponding Japanese Application No. 2019-550487 dated Sep. 10, 2021, and its English translation.

Kink and Williams, "Antibodies to Recombinant Clostridium difficile Toxins A and B Are an Effective Treatment and Prevent Relapse of C. difficile-Associated Disease in a Hamster Model of Infection", Infection and Immunity, vol. 66, No. 5, May 1998, 2018-2025.

Hirai et al., "Passive Oral Immunization by Egg Yolk Immunoglobulin (IgY) to Vibrio cholerae Effectively Prevents Cholera", Acta Medica Okayama, vol. 64, Issue 3, Jun. 2010, 163-170.

Guimaraes et al., "Growth inhibition of *Staphylococcus aureus* by chicken egg yolk antibodies", Archivum Immunologiae et Therapiae Experimentalis, 57 (2009), 377-382.

First Office Action for corresponding Japanese Application No. 2022-077019 mailed Apr. 21, 2023 and its English language Machine Translation.

First Office Action and Search Report for Corresponding Chinese Application No. 201880081696.1 dated Mar. 13, 2023 and its English language Translation.

First Office Action for corresponding Japanese Application No. 2023-124345 dated Aug. 29, 2024 and its English Machine Translation.

Second Office Action for corresponding Japanese Application No. 2023-124345 mailed Mar. 25, 2025 and its English Machine Translation.

* cited by examiner

C. difficile Toxin A concentration

C. difficile Toxin B concentration

Time after toxin administration (minutes)

Time after toxin administration (minutes)

□Pre–immune IgY    ■Ostrich IgY against CT

Absorbance (450 nm)

Dilution factor

CT (100 μg/animal)
+
Pre-immune (14 mg/animal)

CT (100 μg/animal)
+
Ostrich IgY (14 mg/animal)

Pre-immune IgY candy (example of 3 hamsters)

Anti-CT IgY candy (example of 3 hamsters)

OSTRICH ANTIBODY FOR BACTERIAL INFECTIOUS DISEASES

TECHNICAL FIELD

The present invention relates to an ostrich antibody-containing composition for treating a bacterial infectious disease and a method for treating a bacterial infectious disease using ostrich antibodies.

BACKGROUND ART

Although development of antibiotics has been advanced, bacterial infectious diseases remain one of the important subjects to be treated. Further, agent-resistant bacteria which acquire resistance to antibiotics appeared in recent years and infectious diseases of the bacteria have become a problem.

SUMMARY OF INVENTION

Solution to Problem

The present inventor unexpectedly discovered that antibodies obtained from an ostrich administered with components derived from a bacterium as immunogens are effective for treating a bacterial infectious disease, thereby completed the present invention. Surprisingly, an ostrich antibody has a significantly better therapeutic effect than an antibody obtained from a bird using the same immunogen as described in the Examples. Furthermore, it was unexpectedly revealed that an ostrich antibody also exerts an effect on an infection due to an agent-resistant bacterium derived from bacterium used as an immunogen. Further, it was unexpectedly revealed that the ostrich antibody of the present invention exhibits an excellent stability in the gastrointestinal tract. Furthermore, it was also unexpectedly revealed that the ostrich antibody of the present invention exhibits an excellent stability when formulated as a candy.

The present invention provides the following items.

(Item X1)

A composition for treating an infectious disease of a gastrointestinal tract infectious bacterium, comprising ostrich antibodies, wherein immunogens of the antibodies are components derived from the bacterium.

(Item X2)

The composition of item X1, wherein the bacterium is selected from the group consisting of *Clostridium difficile, Vibrio cholera, Staphylococcus aureus, Pseudomonas aeruginosa,* Enterobacteriaceae, *Enterococcus faecium, Helicobacter pylori, Campylobacter, Salmonella,* and *Shigella.*

(Item X3)

The composition of item X1 or 2, wherein the infectious disease is a gastrointestinal tract infectious disease.

(Item X4)

The composition of item X1 or 2, wherein the infectious disease includes an infectious disease in at least one location of a stomach, a duodenum, a small intestine, a large intestine, a rectum, and an anus.

(Item X5)

The composition of any one of items X1 to 4, wherein the components derived from the bacterium include a microbial cell, a homogenate, a toxin, an enzyme, a polysaccharide, a pigment, a cell wall, a cytoplasm, a spore, a flagellum, a fimbria of the bacterium, or a part thereof, or any combination thereof.

(Item X6)

The composition of any one of items X1 to 5, wherein the bacterium includes *Clostridium difficile.*

(Item X7)

The composition of item X6, wherein the immunogen includes at least one of *Clostridium difficile* toxin A and toxin B.

(Item X8)

The composition of any one of items X1 to 5, wherein the bacterium includes *Vibrio cholera.*

(Item X9)

The composition of item X8, wherein the immunogen includes *Vibrio cholera* toxin.

(Item X10)

The composition of any one of items X1 to 5, wherein the bacterium includes *Staphylococcus aureus.*

(Item X11)

The composition of item X10, wherein the immunogen includes a homogenate of *Staphylococcus aureus.*

(Item X12)

The composition of any one of items X1 to 11, wherein the infectious disease is due to an agent-resistant bacterium of the bacterium.

(Item X13)

The composition of item X12, wherein the components derived from the bacterium include a homogenate of the bacterium.

(Item X14)

The composition of item X13 dependent from item X8, wherein the bacterium includes methicillin-resistant *Staphylococcus aureus.*

(Item X15)

The composition of any one of items X1 to 14, wherein the composition is a pharmaceutical composition.

(Item X16)

The composition of item X15, wherein the composition is a pharmaceutical composition for oral administration.

(Item X17)

The composition of any one of items X1 to 14, wherein the composition is a food composition.

(Item X18)

The composition of any one of items X1 to 17, wherein the composition is a candy.

(Item Y1)

A composition for treating an infectious disease of a bacterium, comprising ostrich antibodies, wherein immunogens of the antibodies are components derived from the bacterium.

(Item Y2)

The composition of item Y1, wherein the infectious disease is a gastrointestinal tract infectious disease.

(Item Y3)

The composition of item Y1 or 2, wherein the components derived from the bacterium include a microbial cell, a homogenate, a toxin, a cytoplasm, a cell wall of the bacterium, or any combination thereof.

(Item Y4)

The composition of any one of items Y1 to 3, wherein the bacterium is *Clostridium difficile.*

(Item Y5)

The composition of item Y4, wherein the immunogens are *Clostridium difficile* toxin A and/or toxin B.

(Item Y6)

The composition of any one of items Y1 to 3, wherein the bacterium is *Vibrio cholera.*

(Item Y7)

The composition of item Y6, wherein the immunogens are *Vibrio cholera* toxin.

(Item Y8)

The composition of any one of items Y1 to 3, wherein the bacterium is *Staphylococcus aureus*.

(Item Y9)

The composition of item Y8, wherein the immunogens are a homogenate of *Staphylococcus aureus*.

(Item Y10)

The composition of any one of items Y1 to 9, wherein the infectious disease is due to an agent-resistant bacterium of the bacterium.

(Item Y11)

The composition of item Y10, wherein the components derived from the bacterium are a homogenate of the bacterium.

(Item Y12)

The composition of item Y10 dependent from item Y8, wherein the bacterium is methicillin-resistant *Staphylococcus aureus*.

(Item Y13)

The composition of any one of items Y1 to 12, wherein the composition is a pharmaceutical composition.

(Item Y14)

The composition of item Y13, wherein the composition is a pharmaceutical composition for oral administration.

(Item Y15)

The composition of any one of items Y1 to 12, wherein the composition is a food composition.

(Item Y16)

The composition of any one of items Y12 to 15, wherein the composition is a candy.

Advantageous Effects of Invention

The antibody of the present invention obtained from an ostrich administered with components derived from a bacterium as immunogens can be effective for treating a bacterial infectious disease. Further, the ostrich antibody of the present invention can be also useful for an infectious disease due to an agent-resistant bacterium.

BRIEF DESCRIPTION OF DRAWINGS

FIG. 8A shows the result of hamsters administered with Pre-immune IgY and CT while FIG. 8B shows the result of hamsters administered with ostrich IgY immunized with CT and CT.

FIG. 9A shows the result of hamsters administered with a Pre-immune IgY candy and CT while FIG. 9B shows the result of hamsters administered with an ostrich IgY candy immunized with CT and CT.

DESCRIPTION OF EMBODIMENTS

Figure 1:
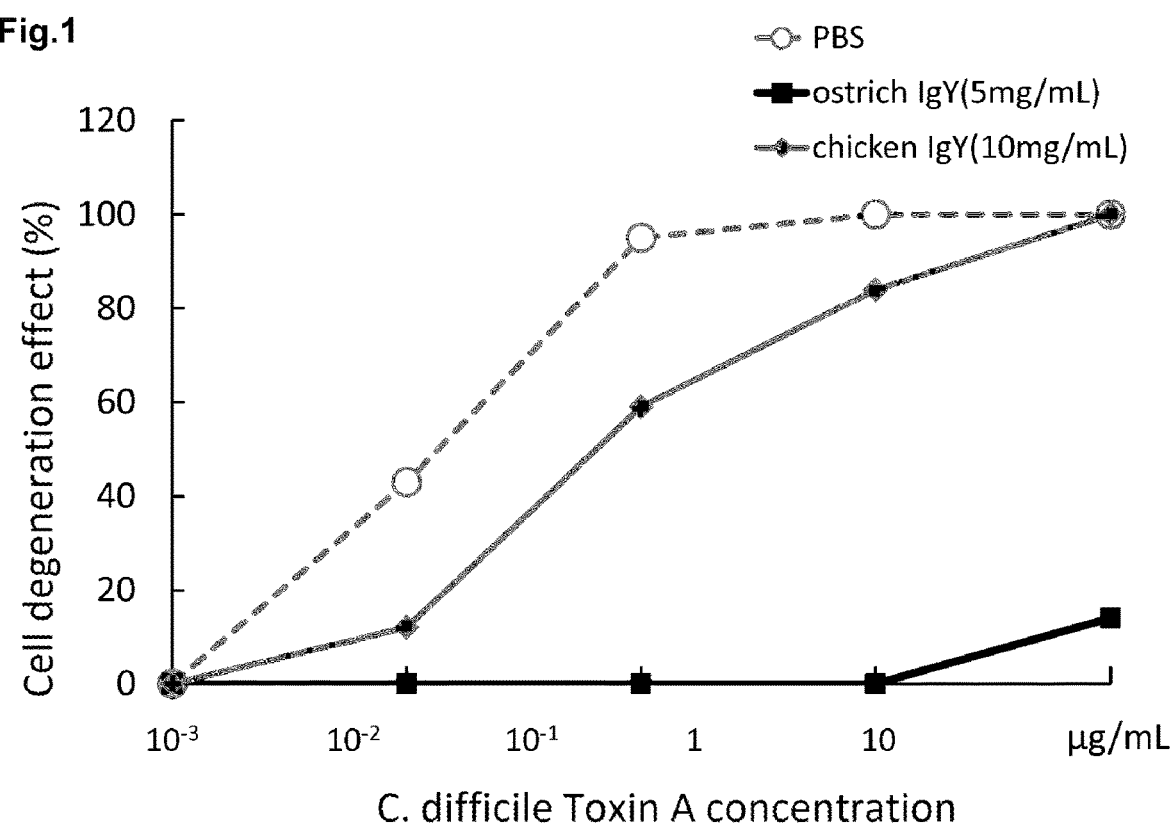
FIG. 1 shows the effect of an ostrich IgY antibody and a chicken IgY antibody on cell degeneration of 3T3 cells due to *Clostridium difficile* toxin A.

The present invention is explained hereinafter with reference to the best embodiments. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

The definitions and/or basic technical contents of the terms particularly used herein are appropriately explained hereinafter.

(Definition)

As used herein, "or" is used when "at least one or more" of the matters listed in a sentence can be employed. The same applies to "or". As used herein, when "within the range" of "two values" is explicitly described, the range also encompasses the two values themselves.

As used herein, "about" refers to variation up to ±10% of a shown value being allowed.

As used herein, "treating" a disease encompasses the concept of both prevention and therapy of the disease.

As used herein, "subject" means any human or non-human animal. For example, the method and composition of the present invention can be used for therapy of a subject suffering from a bacterial infectious disease or prevention for a subject at risk of suffering from a bacterial infectious disease.

As used herein, "immunogen" refers to a target substance, wherein an antibody binding to said target substance is to be obtained. An immunogen can be, for example, a cell, intracellular component, an extracellular component, a cell membrane, a cell wall, a secretion of an organism, or an allergy substance or the like. As used herein, an immunogen may be purified or unpurified.

As used herein, an "agent-resistant bacterium" of a certain bacterium refers to a bacterium in which said certain bacterium acquired resistance to an agent (in particular, antibiotic) effective for said certain bacterium due to a mutation or the like.

(Ostrich Antibody)

The ostrich antibody of the present invention can be an IgY antibody obtained by inoculating a female ostrich using components derived from a bacterium as immunogens and collecting the antigen from the egg yolk of the ostrich. As used herein, an antibody obtained by using a certain substance as an immunogen encompasses an antigen produced when administering said substance to an ostrich, and an antigen produced by modifying the above antibody without changing the antigen binding. For example, an antibody modified in this manner includes, but is not limited to, an antibody modified without changing CDR and an antibody in which only the constant domain has been modified. Those skilled in the art can make such an antibody using any well-known technique. Further, as long as a substance which is an immunogen is identified, those skilled in the art can readily identify which antibody is an antibody obtained by using this substance as an immunogen. In one embodiment, the antibody of the present invention may be an antibody produced by further modifying an antibody produced from an ostrich.

In one embodiment, the antibody of the present invention may be polyclonal antibodies, wherein the polyclonal antibodies may be antibodies obtained by using a single substance (e.g., single species of microorganism, single species of protein, or the like) as an immunogen, or may be antibodies obtained by using a plurality of substances (e.g., a plurality of species of microorganisms, a plurality of species of proteins in a single species of microorganism, or the like) as an immunogen. In one embodiment, the antibody of the present invention may be a specific one or plurality of species of antibodies which were isolated, purified or concentrated. In one embodiment, the antibody of the present invention or at least one type of the antibody of the present invention binds to or specifically binds to an immunogen used when obtaining said antibody or a component thereof.

A component derived from a bacterium can be any component derived from a bacterium, can be typically an unprocessed microbial cell, a bacterial homogenate, a toxin, an enzyme, a polysaccharide or a pigment produced by a bacterium, a cell wall or a cytoplasm, a spore, a flagellum or a fimbria of a bacterium, or a part thereof, and can be preferably a homogenate or a toxin of a bacterium. A component derived from a bacterium as an immunogen is preferably a homogenate. A component derived from a bacterium as an immunogen can be preferably a toxin produced by a bacterium, e.g., an endotoxin, an exotoxin, a capsule, a spore. For example, a bacterial component includes enterotoxin, TSST-1, coagulase, protease, lipase, protein A, pyocyanin, pyoverdine, pyorubin, exotoxin A, hemolysin, alkaline peptidase, elastase, exoenzyme S, rhamnolipid, mold toxin: mycotoxin, and the like. The antibody of the present invention or at least one species of the antibody of the present invention can bind or specifically bind to any of these compounds. For treating an infectious disease due to an agent-resistant bacterium, an ostrich antibody of which immunogen is a homogenate of the bacterium can be preferred.

In a preferred embodiment, the antibody used in the composition of the present invention can be antibodies obtained by immunizing an ostrich with a homogenate, toxin A and/or toxin B of *Clostridium difficile* as an immunogen. In another preferred embodiment, the antibody used in the composition of the present invention can be antibodies obtained by immunizing an ostrich with a homogenate and/or cholera toxin of *Vibrio cholera* as an immunogen. In another preferred embodiment, the antibody used in the composition of the present invention can be antibodies obtained by immunizing an ostrich with a homogenate and/or cholera toxin of *Staphylococcus aureus* as an immunogen.

In one embodiment of the present invention, an immunogen can be obtained by homogenizing a microbial cell or an allergen in phosphate buffer solution (PBS) by a homogenizer. Homogenization can be performed at pH about 6 to about 8, preferably at pH about 7 under refrigeration (4 degrees). A high speed rotation machine for extracting protein can be used for a homogenizer. Preferably, the liquid is directly used as an immunogen to immunize aves without centrifuging liquid the after homogenization. Although a protease inhibitor or a stabilizer is not used, trehalose may be added so as to be 4% of the liquid. Furthermore, the liquid obtained in this manner may be mixed with an adjuvant for immunization, but an antibody can be produced even without using an adjuvant.

The present invention can also provide a method for manufacturing an ostrich antibody which is useful for treating a bacterial infectious disease. The antibody of the present invention can be obtained from a female ostrich using a known method. Upon immunization, any additive component such as adjuvant, salt and stabilizer can be utilized with an immunogen. Further, upon immunization, an immunogen can be administered under any optimal condition (e.g., dosage, administration site, pH, temperature or the like). Regarding immunization, booster may be performed after priming.

Immunization of an ostrich is typically performed in, but not limited to, the following manner.

Priming: An immunogen is mixed with an appropriate adjuvant such as Freund's Complete Adjuvant, and the mixture is inoculated into the muscle of the loin of a female ostrich.

Booster: After priming, booster is performed three times every other week. An immunogen is mixed with an appropriate adjuvant such as Freund's Incomplete Adjuvant, and the mixture is inoculated into the muscle of the loin of the female ostrich.

Antibodies are purified from an ostrich egg laid after week 2 of the booster.

(Bacterial Infectious Disease)

The ostrich antibody of the present invention is produced from an ostrich using components derived from a bacterium as immunogens and can be useful for treating an infectious disease due to said bacterium.

The bacterium causing an infectious disease in which the ostrich antibody of the present invention is useful for treating said disease includes, but is not limited to, *Clostridium difficile* (*C. difficile*), *Vibrio cholera* (*V. cholera*), *Staphylococcus aureus* (*S. aureus*), *Acinetobacter bau-*

*mannii, Pseudomonas aeruginosa*, Enterobacteriaceae, *Enterococcus faecium, Helicobacter pylori, Campylobacter, Salmonella*, gonococcus, *Streptococcus pneumoniae, Shigella, Haemophilus influenzae, Mycobacterium tuberculosis* and the like. Since the ostrich antibody of the present invention can be delivered to the entire gastrointestinal tract (including the stomach, the small intestine and the large intestine) while retaining the activity even when orally administered, said ostrich antibody can provide effective treatment through oral administration for an infectious disease due to a bacterium forming a nidus deeply in the gastrointestinal tract (such as the stomach, the small intestine or the large intestine). Therefore, the present invention effectively treats a gastrointestinal tract infectious bacterium (e.g., the above bacteria) particularly in the form of oral administration. In one embodiment, the bacterium treated by the antibody of the present invention is a gastrointestinal tract infectious bacterium selected from the group consisting of *Clostridium difficile, Vibrio cholera, Staphylococcus aureus* (e.g., agent-resistant *S. aureus*), *Pseudomonas aeruginosa*, Enterobacteriaceae, *Enterococcus faecium, Helicobacter pylori, Campylobacter, Salmonella*, and *Shigella*.

The ostrich antibody of the present invention can be useful for a gastrointestinal tract infectious disease. This is because the ostrich antibody of the present invention can be added to food (including drink) and can easily access the gastrointestinal tract as explained hereafter. However, the use of the ostrich antibody of the present invention is not limited to a gastrointestinal tract infectious disease. In one embodiment, the antibody of the present invention can be intended for treating a bacterial infectious disease in at least one location of inside a mouth, an esophagus, a throat, a stomach, a duodenum, a small intestine, a large intestine, a rectum, and an anus. In a preferred embodiment, the antibody of the present invention can be intended for treating a bacterial infectious disease in at least one location of a stomach, a duodenum, a small intestine, a large intestine, a rectum, and an anus. Further, the ostrich antibody of the present invention can be administered in any dosage form including tablet, liquid, injection, skin application drug, collunarium, instillation, oral cavity spray, washing drug and the like.

The ostrich antibody of the present invention can be useful for not only an infectious disease due to a bacterium but also for an agent-resistant bacterium derived from said bacterium which acquired agent-resistance. There are some mechanisms of agent-resistance acquisition of an agent-resistant bacterium, but typical mechanisms include acquisition of the ability of producing an agent decomposing enzyme or modifying enzyme, mutation in an agent acting site, decrease in the holes through which an agent invades a microbial cell, acquisition/enhancement of an agent efflux mechanism and the like. Although not intending to be bound by any theory, since the ostrich antibody of the present invention can suppress growth or infectious diseases of a bacterium by a mechanism different from these resistance acquisition mechanisms, it is considered that an ostrich antibody made by using a certain bacterium as an immunogen also exerts an effect on an agent-resistant bacterium derived from said bacterium. Alternatively, it is considered that the ostrich antibody of the present invention is an ostrich antibody which binds to and neutralizes a protein synthesis enzyme (e.g., enzyme for bacterial growth), an agent decomposing enzyme or the like that is acquired and produced by a bacterium through mutation for resistance to an antibiotic/agent.

Thus, although the Examples below describe specific examples in which an ostrich antibody made by using *S. aureus* as an immunogen was also effective for methicillin-resistant *S. aureus*, those skilled in the art readily understand that the present invention is not limited to said examples and the principle of the present invention can apply to any bacterium and any agent-resistant bacterium derived from the bacterium.

(Medicament and Administration Thereof)

The present invention also provides a method for treating a bacterial infectious disease of a subject, the method comprising a step of administering the subject with ostrich antibodies made by using the bacterium as an immunogen.

It is understood that as used herein, "medicament" is interpreted in the broadest sense in the art, encompasses any drug, is used as a concept encompassing not only drugs applied to humans but also drugs applied to animals (veterinary medicament) as well as pharmaceutical products, quasi drugs and the like under the Pharmaceutical Act, and encompasses agents, compositions and the like of any use intended for therapy or prevention of a disease, a disorder or a condition in need of a probiotic, prebiotic or symbiotic effect such as improvement in the intestinal bacterial flora balance utilizing said effect. Such examples include application in the medical field, the veterinary science or the like. A medicament normally can contain a solid or liquid excipient and contain, as required, an additive such as a stabilizer, a pH regulator, a solidifying agent (e.g., millet jelly), a disintegrating agent, a flavoring agent, a delayed release agent, a lubricant, a binder or a colorant. The form of a pharmaceutical product includes, but is not limited to, candy, tablet, injection, capsule agent, granular agent, powdered agent, fine granular agent, sustained release formulation and the like. The component, the microorganism, the compound, the probiotics, the prebiotics or the symbiotics and the like of the present invention can be configured to be a pharmaceutical composition in combination with an ingredient such as a pharmaceutically acceptable common carrier or excipient.

The antibody of the present invention can be administered to a mammal, preferably a human, in any pharmaceutically acceptable administration form as a bolus or through continuous infusion over a certain period via an intramuscular route, an intraperitoneal route, an intracerebral route, a subcutaneous route, an intraarticular route, an intrasynovial route, an intrathecal route, an oral route, a topical route or an inhalation route. The present invention is particularly useful for a gastrointestinal tract infectious disease. Oral administration, which easily exerts an action on the gastrointestinal tract, is particularly preferred for treating a gastrointestinal tract infectious disease. In one embodiment, oral administration of the antibody of the present invention can exert a therapeutic effect on inside a mouth, an esophagus, a throat, a stomach, a duodenum, a small intestine, a large intestine, a rectum, and an anus. In one embodiment, the ostrich antibody of the present invention can be particularly suitable for use through oral administration because said ostrich antibody, when orally administered, can exhibit an unexpected property in which a sufficient amount is not decomposed and the antibody can remain active even in the gastrointestinal tract following the stomach (e.g., small intestine and large intestine). Furthermore, the ostrich antibody can be applied to bacteremia, toxemia or the like from the gastrointestinal tract (e.g., through injection of an ostrich antibody).

An appropriate dosage of the antibody of the present invention can depend on the type, seriousness and process of a bacterial infectious disease to be treated, which of prevention and therapy the administration of the antibody is intended for, the therapy in the past, the medical history and response to the antibody of a subject, and the discretion of an attending physician. The antibody of the present invention can be appropriately administered to a patient at one time or over a series of treatments.

Regarding the ostrich antibody of the present invention, about 1 µg/kg to about 20 g/kg of the antibody can be the first candidate dosage to be administered to a patient depending on the type and seriousness of an infectious disease.

The antibody of the present invention may be administered in combination with other agent(s) (e.g., antibiotics) useful for treating a bacterial infectious disease. Other agent(s) include(s), but are (is) not limited to, β lactam based (penicillin based, based), cephem aminoglycoside based, macrolide based, tetracycline based, quinolone based, clindamycin based, gentamicin based, chloramphenicol based, mitomycin based, vancomycin based, methicillin based, nystatin based, carbapenem based, amphotericin based, polyether based, peptide based antibiotics, sulfonamide based, nitrofuran based, isonicotinic acid hydrazide based, pyrazinamide based, arsenic compound based, antimony compound based, quinoline compound based chemotherapeutic drugs and the like.

(Food)

As used herein, "food" has a meaning ordinarily used in the art, refers to every foodstuff (including drink) that humans can eat, and can include a processed product as one embodiment. For example, the component, the microorganism, the compound, the probiotics, the prebiotics or the symbiotics or the like of the present invention can be mixed with a processed food such as confectionery, a dairy product or a cereal processed product. Further, "healthy food" and "functional food" have a meaning commonly used in the industry and refer to a type of food specially formulated for probiotics, prebiotics or symbiotics for improvement in the intestinal bacterial flora balance or the like, which is distinguished from a pharmaceutical product or a common food. Examples of such a food can be expected to be, but are not limited to, for example a food that a subject is allowed to intake before a meal or along with a meal for a certain period. The food of the present invention can also include drink.

In one embodiment, since the present invention is intended for treating (therapy, prevention, a or both thereof) gastrointestinal tract infectious disease, it is preferable that the present invention is contained in a food such that the antibody exerts an efficacy in the gastrointestinal tract.

In one preferred embodiment, the antibody of the present invention can be orally administered to a subject through a candy.

Particularly for ostriches, an egg yolk antibody is resistant to acidity or alkalinity and is highly heat resistant. Specifically, it should be noted that antibody activity can be maintained even at 120° C. Antibody activity can be also maintained in an intragastric low pH environment and antibody activity can be also maintained in a small intestinal alkali environment. The present inventor discovered that the ostrich antibody of the present invention that was orally administered can be active even in excrements. It was unexpectedly discovered that antibody activity can be retained in excrements despite a severe pH environment in the stomach and the small intestine and various types of protein decomposing enzymes present in the gastrointestinal tract (e.g., stomach and small intestine). In one embodiment, the ostrich antibody of the present invention prepared as a candy retain an immunogen binding property of at least 95%, at least 90%, at least 80%, at least 70%, at least 60%, at least 50%, at least 40%, at least 30%, at least 20%, at least 15%, at least 10%, at least 7%, at least 5%, at least 2% or at least 1% as compared to the antibody before prepared as a candy when evaluated by ELISA. Decrease in the immunogen binding property to a certain extent may observed due to preparation into a candy, however, preparation into a candy can be advantageous even in such a case. Further, those skilled in the art can prepare a candy such that activity at a necessary level is obtained while considering decrease in the activity.

The candy of the present invention can be manufactured by, for example, mixing sugar and millet jelly and heating the mixture to produce candy paste, adding a dissolved antibody dissolved with 1 part to 100 parts of water or edible oil and fat relative to 1 part of an ostrich egg yolk antibody to the candy paste while keeping it at 60 to 110° C., kneading the mixture thereof while cooling it until the dissolved antibody is uniformly dispersed over the whole candy paste, then forming the mixture in a desired shape. Resistance to processing at such a high temperature is one of the characteristics of an ostrich antibody. In one embodiment, the ostrich antibody of the present invention can achieve a preservation stability with a longer period by being encapsulated in a candy as compared to, for example, in a solution. Although not wishing to be bound by any theory, the ostrich antibody of the present invention can be stabilized due to the less amount of free water in a candy. Further, the ostrich antibody of the present invention prepared as a candy can be handy for carrying it.

EXAMPLES

Example 1: Reactivity of Egg Yolk Antibodies Made by Immunizing Ostriches and Chickens with *Clostridium difficile* Toxin Antibody Producing Method:

A mixture solution of *Clostridium difficile* toxin A (50 µg) and toxin B (50 µg) (provided by Dr. Ciaran P. Kelly, Harvard University) was mixed with 0.2 mL of Freund's Complete Adjuvant to prime each of mature female ostriches and chickens (five ostriches and five chickens in total were inoculated). It should be noted that the one ostrich and one chicken were inoculated with the same amount of antigens. After priming, each bird was boosted with a mixture solution of the same amount of antigen and Freund's Incomplete Adjuvant as described above in week 2 and week 4. Egg yolk antibodies (IgY) were purified from the egg yolk of eggs from each bird obtained in week 8 after priming. Reactivity of the obtained egg yolk antibodies was tested by ELISA.

ELISA Method:

Solid phases of 10 µg of each toxin were formed separately at each well of a 96-well ELISA plate (4 hours at room temperature). Serially diluted solutions (undiluted solution is 2 mg/mL) of ostrich antibodies (mixture of antibodies from the egg yolk obtained from each 3 ostriches) and chicken antibodies (mixture of antibodies from the egg yolk obtained from each 3 chickens) were then dripped into each well and reacted for 1 hour at room temperature. After washing, HRP labeled-secondary antibodies for each antibody were reacted for 1 hour at room temperature. After thoroughly washing, a luminescent peroxidase assay kit (S-Bio SUMILON) was used to measure absorbance (450 nm) with a plate reader. The maximum dilution factor indicating 2 times the absorbance value or greater of egg yolk antibodies of each avian species prior to immunization are shown as the ELISA value.

Result:

IgY antibodies reacting to toxin A and toxin B were made from the ostriches and chickens. Although each bird was immunized with the same amount of antigens, large-sized ostriches produced antibodies with a high reactivity. This indicates that ostriches can produce highly sensitive antibodies with a small amount of antigens (Table 1). The reactivity of the ostrich antibodies to toxin A was equal to that of the chicken antibodies, while the reactivity of the chicken antibodies to toxin B was higher than that of the ostrich antibodies.

TABLE 1

| | ELISA value | |
| Antigen | Ostrich IgY | Chicken IgY |
| --- | --- | --- |
| C. difficile toxin A | 404,800 | 404,800 |
| C. difficile toxin B | 51,200 | 102,400 |

Example 2: Toxin Neutralization Effect of IgY Antibodies Made by Immunization with *Clostridium difficile* Toxin Neutralization activity (inactivation) of the ostrich antibodies and chicken antibodies made in Example 1 against *Clostridium difficile* toxins A and B was tested in vitro and in experiments on animals using mice.

Neutralization Activity In Vitro:

3T3 cells were cultured in a 96-well microplate and *Clostridium difficile* toxin A with each concentration ($10^{-3}$, $10^{-2}$, $10^{-1}$, 1, 10 µg/mL) was added. Phosphate buffer solution (PBS) or the ostrich IgY (ostrich IgY) (5 mg/ml) or chicken IgY (chicken IgY) (10 mg/mL) against *Clostridium difficile* toxin made in Example 1 was then added to all wells. After 48 hours, the cells were observed under a microscope and the ratio of wells exhibiting a cell degeneration effect was calculated (FIG. 1).

Figure 2:
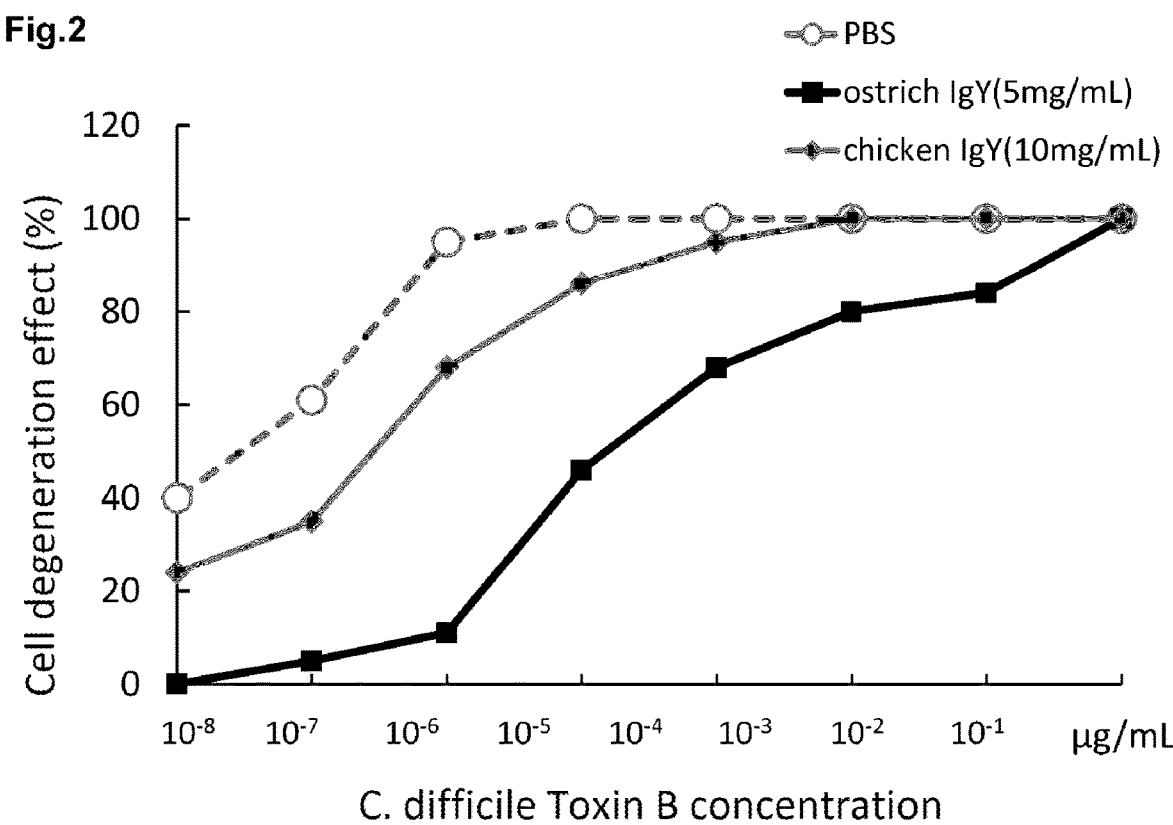
FIG. 2 shows the effect of an ostrich IgY antibody and a chicken IgY antibody on cell degeneration of 3T3 cells due to *Clostridium difficile* toxin A.

In the same manner, 313 cells were cultured in a 96-well microplate and *Clostridium difficile* toxin B with each concentration ($10^{-8}$ to $10^{-1}$ µg/mL) was added. Phosphate buffer solution (PBS) or the ostrich IgY (ostrich IgY) (5 mg/mL) or chicken IgY (chicken IgY) (10 mg/mL) against *Clostridium difficile* toxin made in Example 1 was then added to all wells. After 48 hours, the cells were observed under a microscope and the ratio of wells exhibiting a cell degeneration effect was calculated (FIG. 2).

When a toxin is added to 313 cells, degenerated cells float in a round shape in a well. It was determined that the cell degeneration effect due to the toxin was exerted when 20% or more of the cells floated in a round shape in this manner.

The cell degeneration effect was significantly suppressed for the ostrich IgY as compared to the PBS administered group (control) and the chicken IgY antibodies. There is no significant difference between the ostrich IgY and the chicken IgY in terms of the reactivity to each toxin (ELISA). However, the chicken IgY exhibited almost no effect whereas the ostrich IgY was unexpectedly effective in terms of inactivation (neutralization) of the toxin to the cells.

As a result, the ostrich IgY exhibited an extremely high effect of suppressing cell degeneration, whereas the chicken IgY exhibited almost no suppression effect although the chicken IgY with 2 times the amount of the ostrich IgY was added.

Testing by experiments on animals:

*Clostridium difficile* Toxin A

Figure 3:
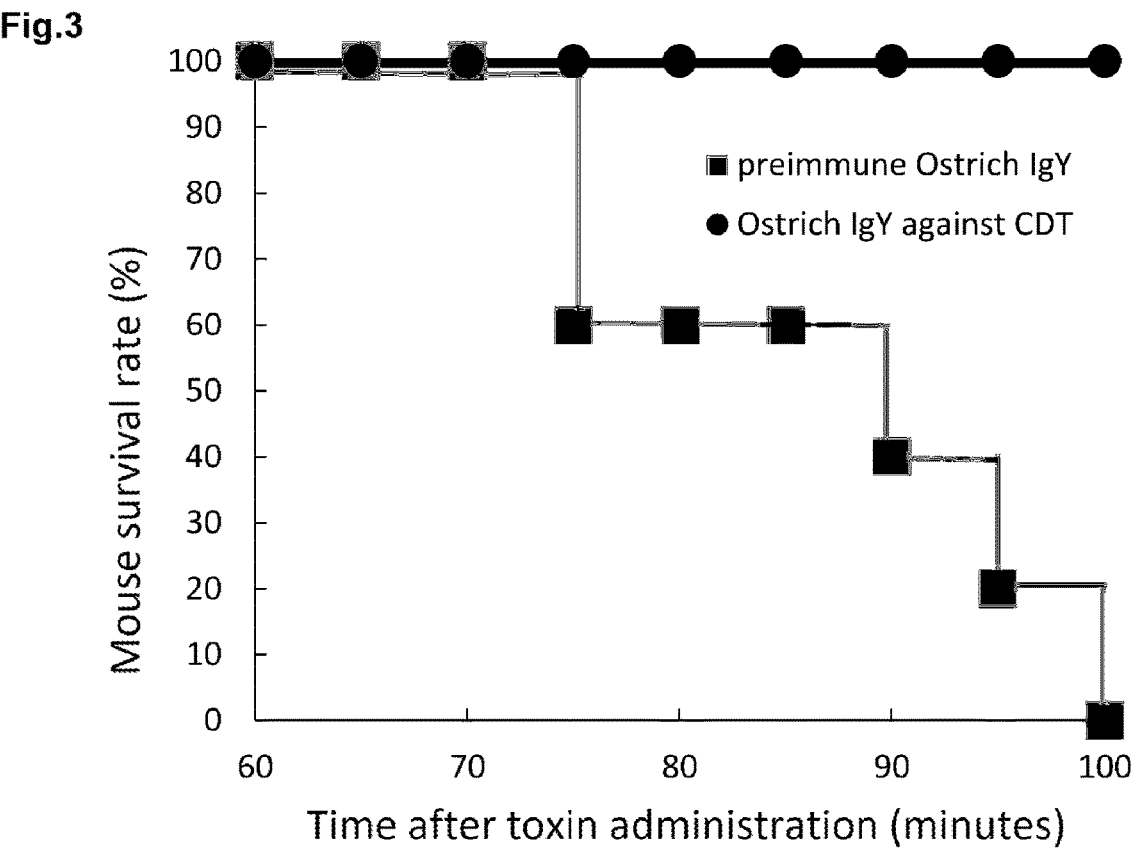
FIG. 3 shows the survival curve after administration of *Clostridium difficile* toxin A in mice inoculated with an ostrich IgY antibody.

C54BL mice (6-week old female mice) were each intraperitoneally administered with 3 mg of preimmune Ostrich IgY (preimmune Ostrich IgY) (negative control) or the Ostrich IgY against *Clostridium difficile* toxin (Ostrich IgY against CDT) made in Example 1 (20 mice for each IgY). After 2 hours, the mice were intraperitoneally administered with a lethal dose of *Clostridium difficile* toxin A (200 ng/mouse) and subsequent viability was recorded over time (FIG. 3). The mice administered with the preimmune IgY were all dead within 100 minutes due to *Clostridium difficile* toxin A, while all of the mice of the ostrich IgY against *Clostridium difficile* toxin administered group survived. That is, it was indicated that the ostrich IgY antibodies made by immunization with *Clostridium difficile* toxin as an immunogen can neutralize (inactivate) *Clostridium difficile* toxin A in the murine body and completely suppress fatality.

Figure 4:
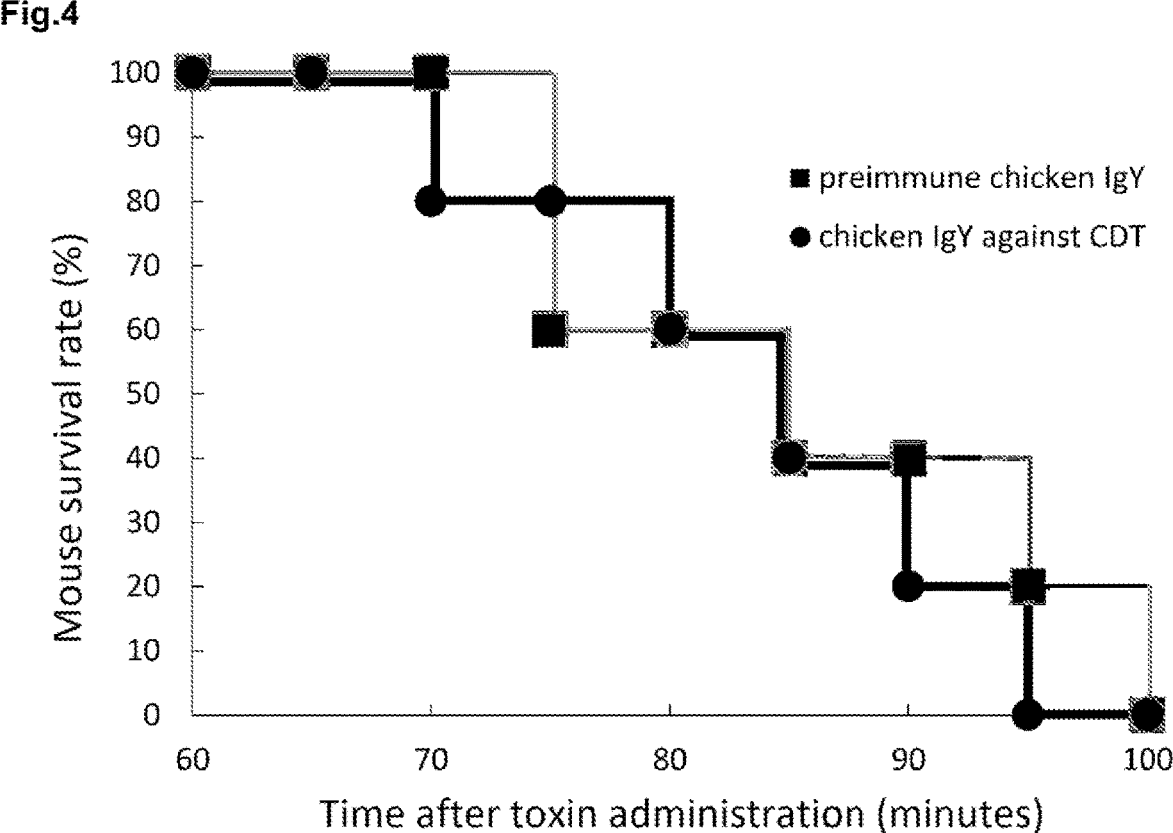
FIG. 4 shows the survival curve after administration of *Clostridium difficile* toxin A in mice inoculated with a chicken IgY antibody.

In the same manner, C54BL mice (6-week old female mice) were each intraperitoneally administered with 6 mg of preimmune chicken IgY (pre-immune Chicken IgY) (negative control) or the chicken IgY against *Clostridium difficile* toxin (chicken IgY against CDT) made in Example 1 (20 mice for each IgY). After 2 hours, the mice were intraperitoneally administered with a lethal dose of *Clostridium difficile* toxin A (200 ng/mouse) and subsequent viability was recorded over time (FIG. 4). Both the mice administered with the preimmune IgY and the mice administered with the chicken IgY against *Clostridium difficile* toxin were all dead within 100 minutes due to *Clostridium difficile* toxin A. That is, it was indicated that the chicken IgY antibodies against *Clostridium difficile* cannot at all suppress fatality due to *Clostridium difficile* toxin A although the mice were administered with said antibodies with 2 times the amount of the ostrich IgY.

Figure 5:
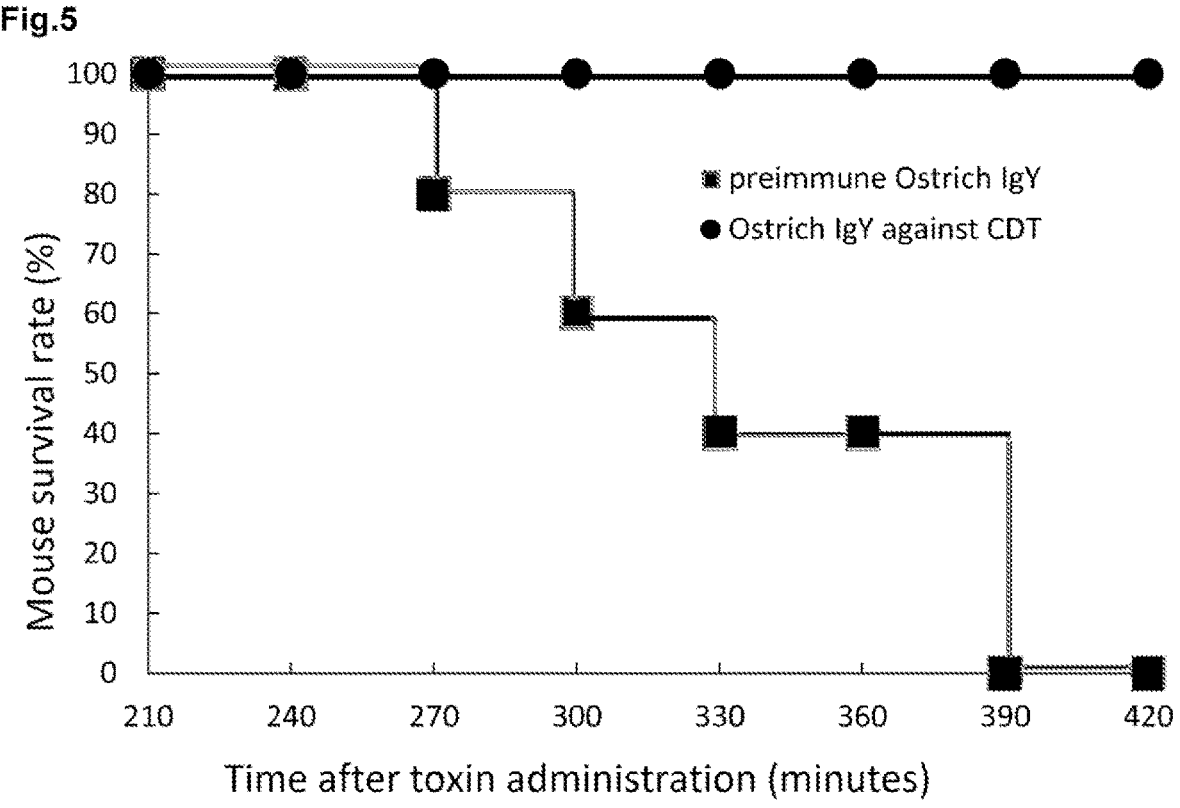
FIG. 5 shows the survival curve after administration of *Clostridium difficile* toxin B in mice inoculated with an ostrich IgY antibody.

*Clostridium difficile* B:

C57BL mice (6-week old female mice) were each intraperitoneally administered with 3 mg of preimmune Ostrich IgY (preimmune Ostrich IgY) (as negative control) or the Ostrich IgY against *Clostridium difficile* toxin (Ostrich IgY against CDT) made in Example 1 (20 mice for each IgY). After 2 hours, the mice were intraperitoneally administered with a lethal dose of *Clostridium difficile* toxin B (200 ng/mouse) and subsequent viability was recorded over time (FIG. 5). The mice administered with the preimmune IgY were all dead within 420 minutes due to *Clostridium difficile* toxin B, while all of the mice administered with the ostrich IgY antibodies made by using *Clostridium difficile* toxin as an immunogen survived. That is, it was indicated that the ostrich IgY antibodies made by using *Clostridium difficile* toxin as an immunogen can neutralize (inactivate) *Clostridium difficile* toxin B in the murine body and completely suppress fatality.

Figure 6:
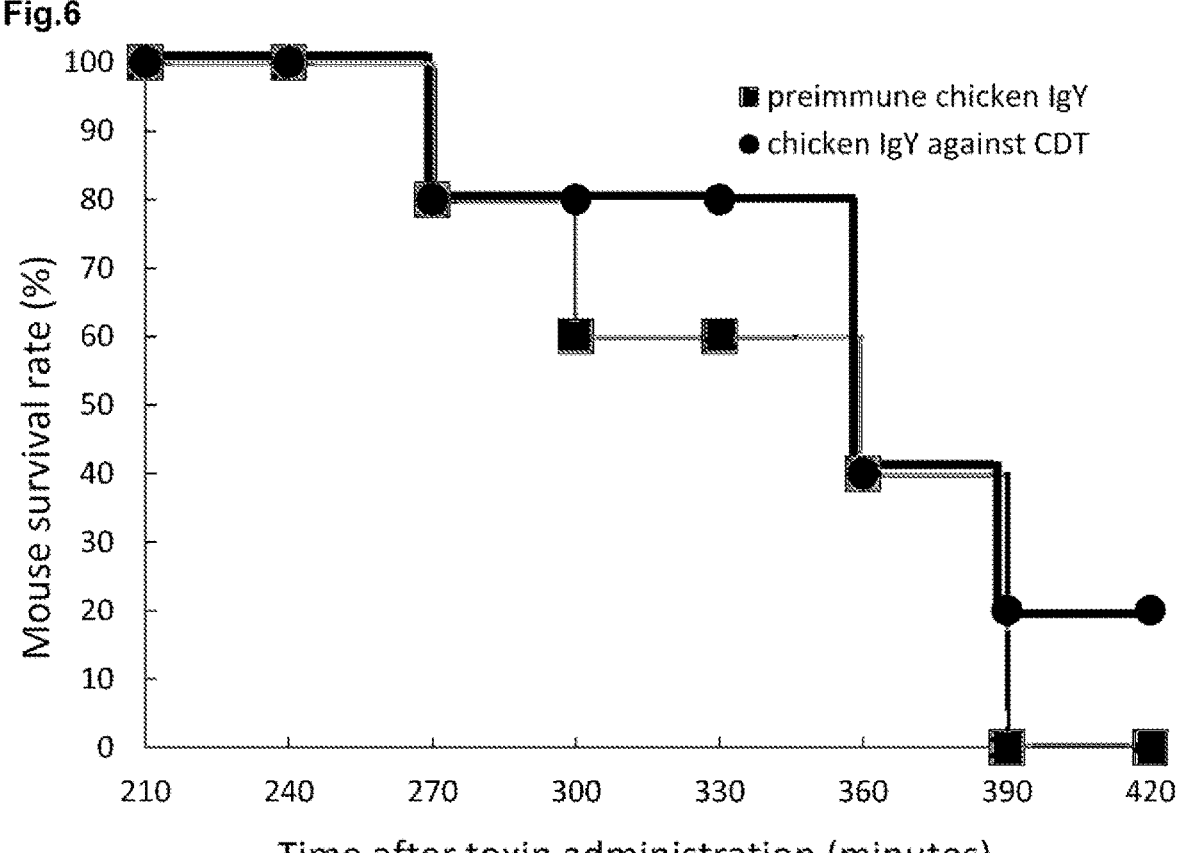
FIG. 6 shows the survival curve after administration of *Clostridium difficile* toxin B in mice inoculated with a chicken IgY antibody.

In the same manner, C54BL mice (6-week old female mice) were each intraperitoneally administered with 6 mg of preimmune chicken IgY (preimmune Chicken IgY) (as negative control) or the chicken IgY against *Clostridium difficile* toxin (chicken IgY against CDT) made in Example 1 (20 mice for each IgY). After 2 hours, the mice were intraperitoneally administered with a lethal dose of *Clostridium difficile* toxin B (200 ng/mouse) and subsequent viability was recorded over time (FIG. 6). The mice administered with the preimmune IgY were all dead within 100 minutes due to *Clostridium difficile* toxin B, while only 20% of the mice administered with the chicken IgY antibodies against *Clostridium difficile* survived in 420 minutes. That is, it was indicated that the chicken IgY antibodies against *Clostridium difficile* exhibit extremely low suppression of fatality due to *Clostridium difficile* toxin B although the mice were administered with said antibodies with 2 times the amount of the ostrich IgY.

In view of the foregoing, intraperitoneal administration of 200 ng of *Clostridium difficile* toxins A and B to the mice results in fatality of 100%, however, when the mice were intraperitoneally administered with the Ostrich IgY (3 mg) before administration of the toxin, both the mice administered with toxin A (FIG. 3) and the mice administered with toxin B (FIG. 5) all survived (i.e., 0% fatality rate). However, when the mice were intraperitoneally administered with the chicken IgY, the fatality rate was 100% for toxin A (FIG. 4) and 20% for B (FIG. 6) even in the amount of 6 mg (2 times the amount of the ostrich IgY). That is, the ostrich IgY can inactivate *Clostridium difficile* toxin in the murine body and have a high prophylactic/therapeutic effect while the chicken IgY exhibited almost no effect, which revealed that the ostrich IgY is unexpectedly excellent.

Example 3: Ostrich IgY Antibodies Made by Immunization with Cholera Toxin

Figures 7, 8A, 8B:
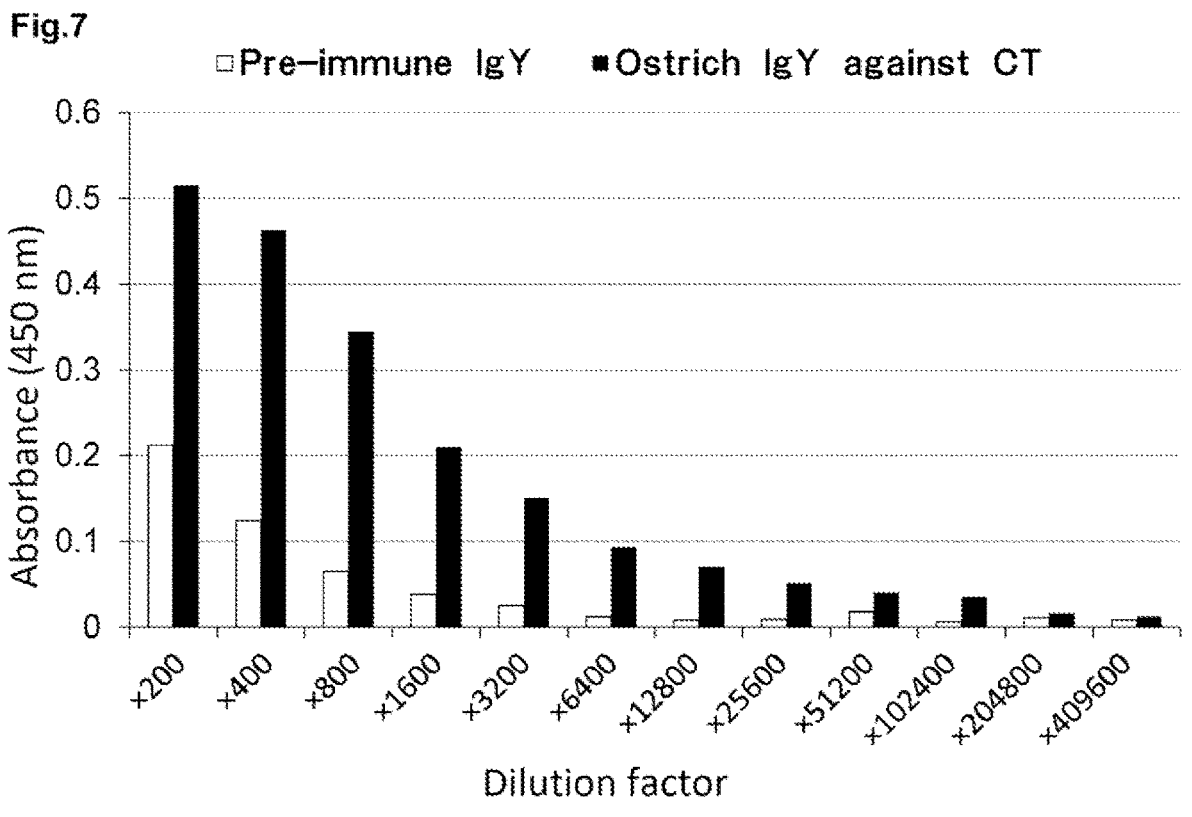
FIG. 7 shows the reactivity of an ostrich IgY antibody of which immunogen is a toxin of *Vibrio cholera* (CT) to CT.
FIGS. 8A and 8B show pathological anatomy pictures of gastrointestinal tract lesions of hamsters administered with an ostrich antibody and CT.

Abstract:

In the present example, an ostrich was immunized with a toxin of *Vibrio cholera* (CT), thereby succeeding in production of highly sensitive anti-CT Ostrich IgY (FIG. 7).

Experiments on animals using hamsters revealed that oral administration of the anti-CT Ostrich IgY can suppress symptoms due to cholera toxin (FIG. 8). Although not wishing to be bound by any theory, it is considered that this is because the Ostrich IgY can undergo an antigen-antibody reaction with cholera toxin and suppress the toxicity thereof the gastrointestinal tract.

Figure 9A:
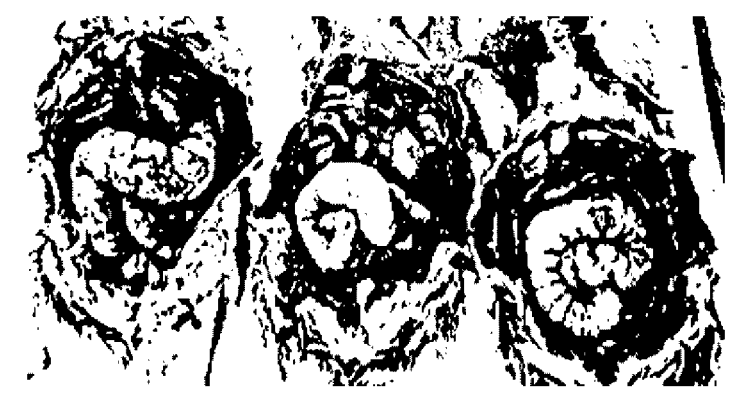
FIGS. 9A and 9B show pathological anatomy pictures of gastrointestinal tract lesions of hamsters administered with an ostrich antibody candy and CT.
Figure 9B:
Figure 10:
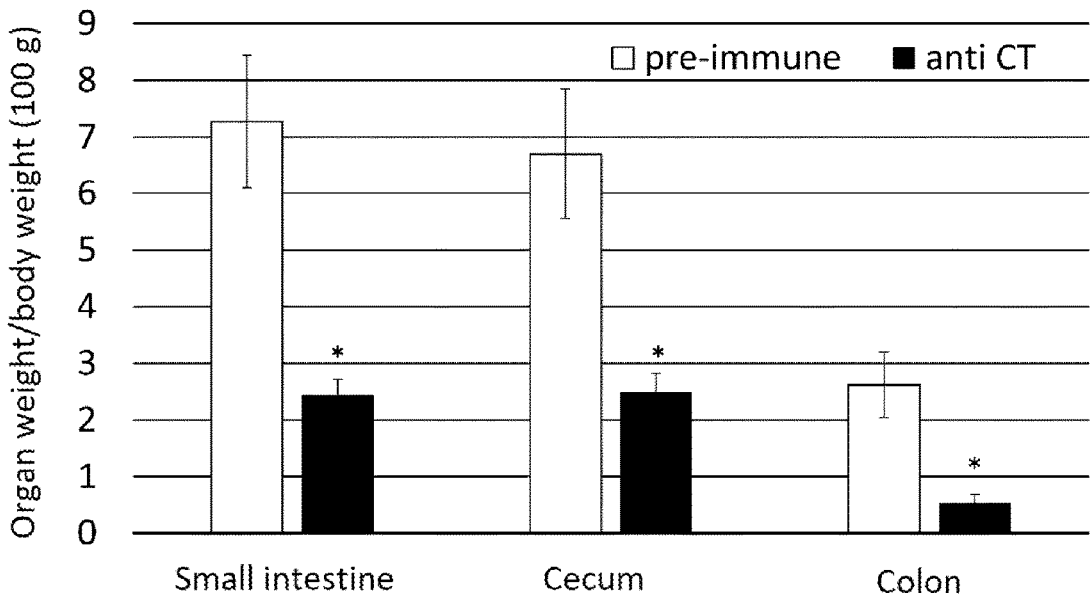
FIG. 10 shows the organ weight of hamsters administered with an ostrich antibody candy and CT.

Further, it was revealed that intake of an ostrich IgY-containing candy can suppress symptoms due to cholera toxin (FIG. 9, FIG. 10). Although not wishing to be bound by any theory, it is considered that this is because IgY from the ostrich IgY candy can undergo an antigen-antibody reaction with cholera toxin and suppress the toxicity in the gastrointestinal tract.

The above results indicate that a large amount of highly sensitive antibodies can be produced from ostriches and further oral intake can suppress symptoms of cholera. Thus, the antibodies are also expected to be in practical use as a food. Further, the antibodies are also expected to be an oral antibody for measures against other gastrointestinal tract infectious disease(s).

Antibody Producing Method:

Mature female ostriches were used. Cholera toxin (CT) (Sigma-Aldrich, Tokyo, Japan) (50 µg) was mixed with 0.2 mL of Freund's Complete Adjuvant to prime one ostrich. After priming, the ostriches were boosted with a mixture solution of the same amount of antigens and Freund's Incomplete Adjuvant as described above in week 2 and week 4. Egg yolk antibodies (IgY) were purified from the egg yolk of eggs from each bird obtained in week 8 after priming. Reactivity of the obtained egg yolk antibodies (IgY) was tested by ELISA.

ELISA Method:

Solid phases of CT (10 µg) were formed separately at each well of a 96-well ELISA plate (4 hours at room temperature). Serially diluted solutions (undiluted solution is 2 mg/mL) of ostrich IgY were then dripped into each well and reacted for 1 hour at room temperature. After washing, HRP labeled-secondary antibodies for each antibody were reacted for 1 hour at room temperature. After thoroughly washing, a luminescent peroxidase assay kit (S-Bio SUMILON) was used to measure absorbance (450 nm) with a plate reader.

Result:

The ostrich IgY made by immunization with CT exhibited a strong reactivity to CT as compared to Pre-immune ostrich IgY (pre-immune IgY) (FIG. 7). Since about 4 g of IgY was purified from one ostrich egg yolk, a large amount of high quality (highly reactive) IgY is produced.

Antibody Administration to Chinese Hamsters:

Mature Chinese hamsters (12-month old female) were orally administered with 14 mg of each of the Pre-immune ostrich IgY (Pre-immune IgY) (negative control) and the Ostrich IgY (Ostrich IgY) made by immunization with cholera toxin (each IgY was administered to 10 hamsters in total). After 10 minutes, each hamster was orally administered with 100 µg of cholera toxin (CT) dissolved in PBS. After 6 hours from CT administration, gastrointestinal tract lesions were evaluated through pathological anatomy.

Result: Dilatation of the gastrointestinal tract (in particular, from duodenum to colon) and retention of water-soluble contents were significantly observed in all of the hamsters administered with the Pre-immune IgY and CT (FIG. 8A). Meanwhile, no lesion (such as dilatation of the gastrointestinal tract) was observed in 90% of the individuals of the hamsters administered with the Ostrich IgY and CT (FIG. 8B).

Conclusion: Oral intake of the ostrich IgY against cholera toxin suppressed the onset due to the toxin upon infection with cholera.

Example 4: Administration Through Candies

Mature Chinese hamsters (12-month old female) were orally administered with 3 g of candies containing Pre-immune ostrich IgY (Pre-immune IgY) (negative control) or the Ostrich IgY made by immunization with cholera toxin in Example 3 (anti CT) (IgY content of 0.2 mg) (each IgY candy was administered to 10 hamsters in total).

The candies were made in the following manner. First, maple syrup was heated to 110° C. to evaporate water. The syrup was cooled to 70° C. and was then added with an ostrich antibody liquid (ostrich IgY liquid against cholera toxin (15 mg/mL, dissolved in phosphate buffer solution)) (the antibody liquid was added so that 0.2 mg of ostrich IgY could be added to 3 g of candies). The mixture thereof was then cooled at a stretch in a refrigerator to be solidified. The sufficiently solidified mixture was cut in 3 g and orally administered to the hamsters.

After 10 minutes, each hamster was orally administered with 100 µg of cholera toxin (CT). After 6 hours from CT administration, gastrointestinal tract lesions were evaluated through pathological anatomy. Further, the weight of each organ was measured to test the mean value, SD and significant difference of 10 hamsters administered with each IgY candy (student t) (* $P<0.05$ significant difference was found).

Result: Dilatation of the gastrointestinal tract (in particular, from duodenum to colon) and retention of water-soluble contents were significantly observed in all of the hamsters administered with the Pre-immune IgY-containing candies and CT (FIG. 9A). Meanwhile, no lesion (such as dilatation of the gastrointestinal tract) was observed in all of the individuals of the hamsters administered with the Ostrich IgY-containing candies immunized with CT and CT (FIG.

9B). Regarding the weight of the organs, oral administration of the ostrich IgY-containing candies made by immunization with CT suppressed the dilatation of each gastrointestinal tract (FIG. 10).

Conclusion: Oral intake of a food containing ostrich IgY against cholera toxin suppressed the onset due to the toxin upon infection with cholera. This indicates the possibility of using said food for an oral prophylactic drug or therapeutic food for cholera infection.

Example 4: Effectiveness of Ostrich Antibodies for Agent-Resistant Bacteria

Two types of bacteria, *Staphylococcus aureus* (*S. aureus*; NBRC102135) and methicillin-resistant *Staphylococcus aureus* (hereinafter, MRSA) (L20A strain JCM16554), were used to consider the possibility of using ostrich antibodies for therapy of infectious diseases due to agent-resistant bacteria.

Culture suspension of *S. aureus* was centrifuged and precipitated. Culture liquid was removed, phosphate buffer solution (pH 7) was added to float bacteria, and bacterial microbial cells were crushed with a homogenizer at 4° C. An ostrich was immunized with this homogenate.
Immunization of Ostrich Priming: 100 μg of each of the above homogenates as protein amount was mixed with Freund's Complete Adjuvant, and the mixture was inoculated into the muscle of the loin of a female ostrich.

Booster: After priming, booster was performed three times every other week. 100 μg of bacterial homogenate liquid was mixed with Freund's Incomplete Adjuvant, and the mixture was inoculated into the muscle of the loin of the female ostrich in each of the above three patterns.

Antibodies were purified from an ostrich egg laid after week 2 of the booster.
Purification of Antibody:

Antibodies from the egg yolk (IgY) were purified in the following manner.

First, to the egg yolk, 5 times the amount of TBS (20 mM of Tris-HCl, 0.15 M of NaCl, 0.5% NaN$_3$) and the same amount of 10% dextran sulfate/TBS were added, and the mixture was stirred for 20 minutes. 1M of CaCl$_2$/TBS was then added in the same amount as the egg yolk, and the mixture was stirred and left standing for 12 hours. The mixture was then centrifuged for 20 minutes at 15000 rpm, and the supernatant was collected. In addition, ammonium sulfate was added such that the final concentration would be 40%, and the mixture was left standing for 12 hours at 4° C. After that, the mixture was centrifuged for 20 minutes at 15000 rpm, and precipitates were collected. Finally, the precipitates in the same amount as the egg yolk were resuspended in TBS, and dialysis was performed with TBS. IgY with a purity of 90% or more was able to be collected by the above step. 2 to 4 g of IgY antibodies were able to be purified from one egg yolk.
*S. aureus* and MRSA Growth Suppression Effect of Ostrich IgY Antibodies Ostrich IgY or phosphate buffer solution (PBS) was mixed with each of the bacterial liquids before culture (*S. aureus* and MRSA) so that the Ostrich IgY or phosphate buffer solution would be 1 mg/mL, and each mixture was cultured in an agar medium (in which 0.1 ml of the bacterial liquid is cultured in a Petri dish with a radius of 10 cm) for 18 hours. Bacterial colonies were counted and PFU (plaque-forming unit) was calculated.

Figure 11:
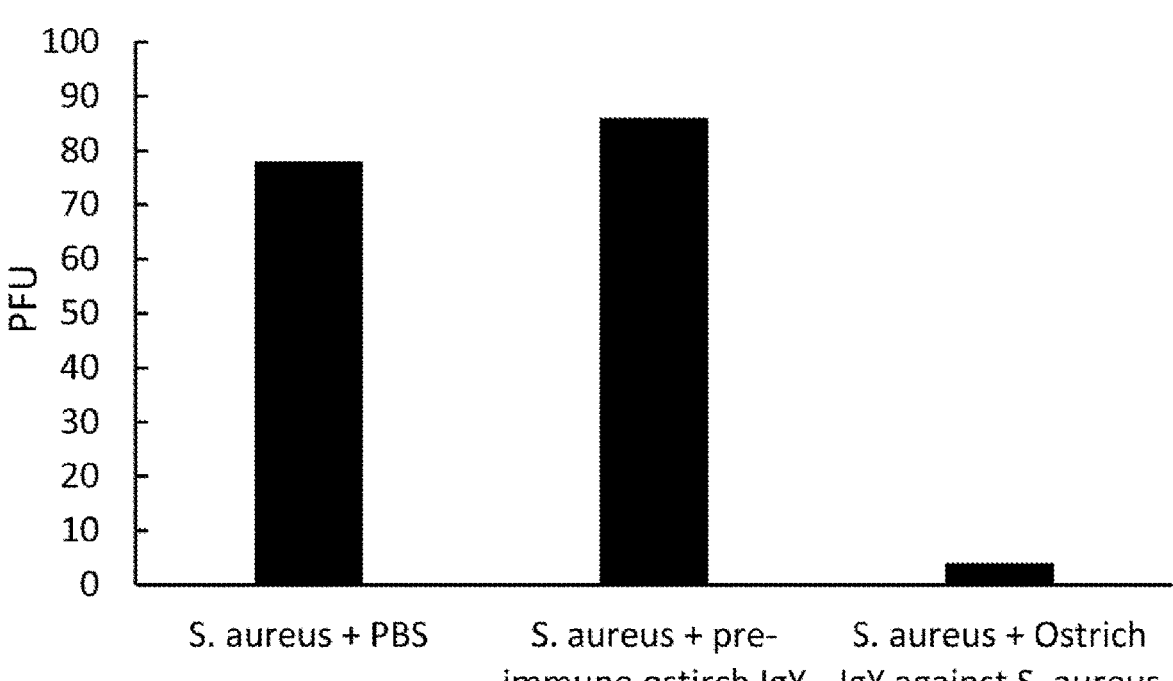
FIG. 11 shows the result of a test of suppressing the growth of *S. aureus* by an ostrich IgY antibody.
Figure 12:
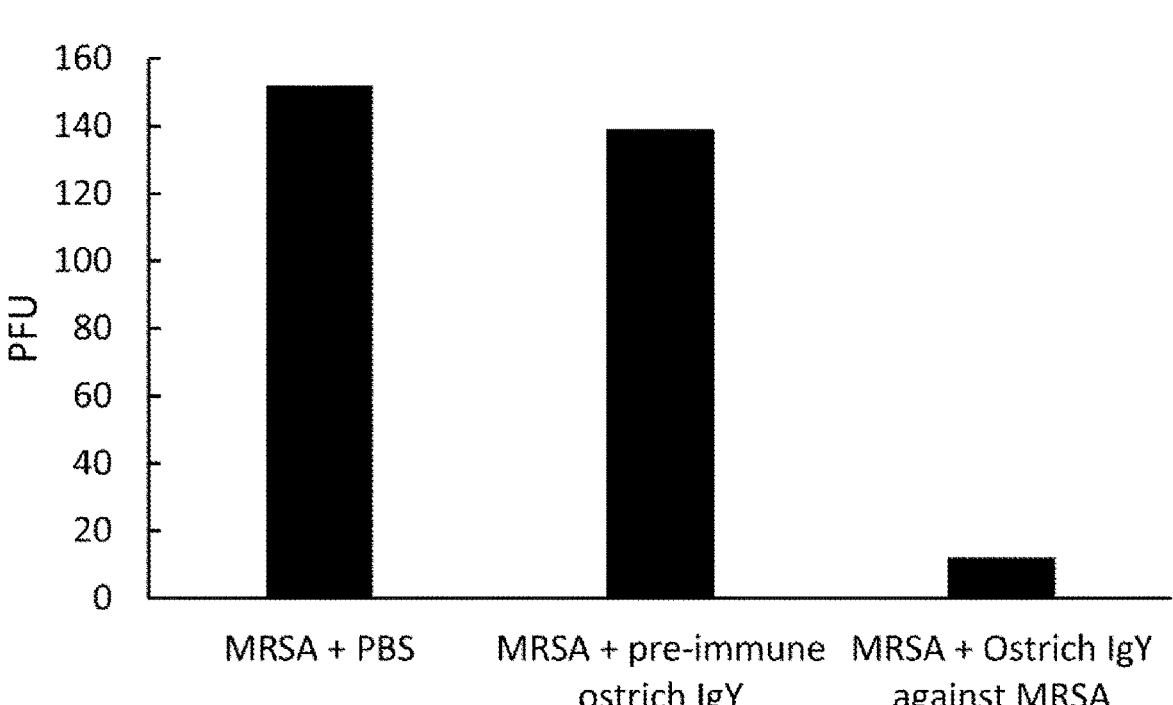
FIG. 12 shows the result of a test of suppressing the growth of MRSA by an ostrich IgY antibody.

Result: It was revealed that the Ostrich IgY made by immunization with *S. aureus* significantly suppresses the growth of not only *S. aureus* (FIG. 11) but also MRSA (FIG. 12). The pre-immune ostrich IgY (pre-immune ostrich IgY) (negative control) exhibited no suppression effect for both *S. aureus* and MRSA. Thus, the possibility that ostrich IgY made by immunization with a bacterium can be expected to be a suppressant of an agent-resistant bacterium such as a multi agent-resistant bacterium.

Comparative Examples: Consideration of Agent-Resistant Bacteria Growth Suppression Effect of Rabbit IgG Antibodies Rabbit IgG made by immunization with a homogenate of *S. aureus* (polyclonal antibody) was used to consider the ability of suppressing the growth of *S. aureus* and MRSA in the same manner as Example 4.
Antibody Producing Method:

Immunization method of a rabbit was the same as that of an ostrich (the same inoculation amount and the same number of times) except for the inoculation location, which is intradermal inoculation in the rabbit hind limb. In month 2 from priming, the whole blood was collected from the rabbit, serum was separated, and IgG was purified with Protein G Column. According to ELISA, the reactivity of the ostrich IgY to the homogenate of *S. aureus* and the reactivity of the rabbit IgG to said homogenate were ELISA value 404,800 and ELISA value 202,400, respectively, which are equal.
*S. aureus* and MRSA Growth Suppression Effect of Rabbit IgG (Polyclonal Antibody)

Rabbit IgG or phosphate buffer solution (PBS) was mixed with each of the bacterial liquids before culture (*S. aureus*, MRSA) so that the Rabbit IgG or phosphate buffer solution would be 10 mg/mL, and each mixture was cultured in an agar medium (in which 0.1 ml of the bacterial liquid is cultured in a Petri dish with a radius of 10 cm) for 18 hours. It should be noted that/mL of 10 times the amount of the Ostrich IgY of Example 4 was used for the test of suppressing the growth of *S. aureus* and MRSA using the Rabbit IgG. Bacterial colonies were counted and PFU (plaque-forming unit) was calculated.

Figure 13:
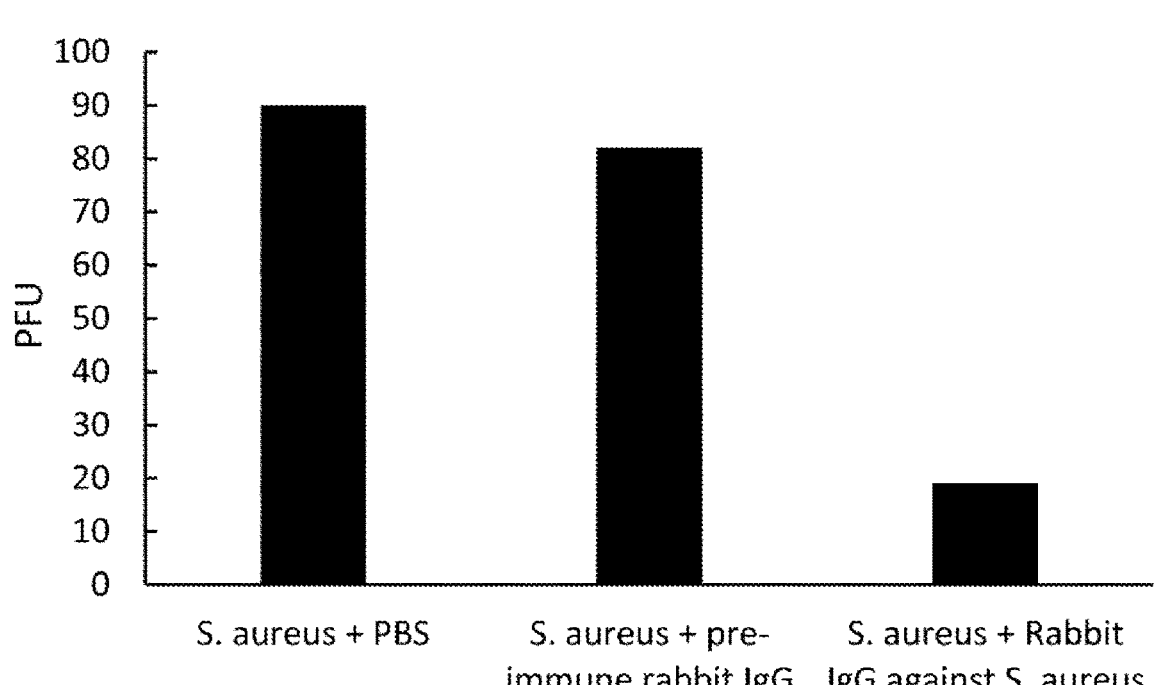
FIG. 13 shows the result of a test of suppressing the growth of *S. aureus* by a rabbit IgG antibody.
Figure 14:
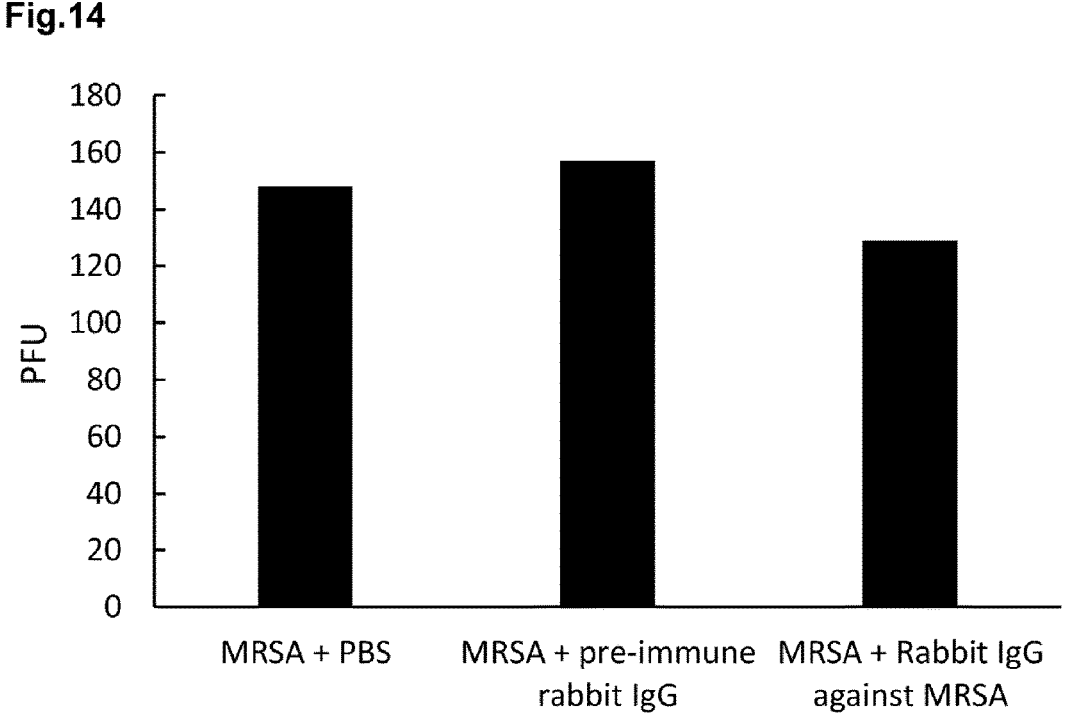
FIG. 14 shows the result of a test of suppressing the growth of MRSA by a rabbit IgG antibody.

Result: The Rabbit IgG made by immunization with *S. aureus* suppressed the growth of *S. aureus* (FIG. 13), whereas the growth of MRSA was not suppressed (FIG. 14). The pre-immune rabbit IgG (pre-immune rabbit IgG) (negative control) exhibited no suppression effect for both *S. aureus* and MRSA. Thus, it was indicated that the phenomenon found in ostrich antibodies in which the antibodies made by using a certain bacterium as an immunogen also have an effect on an agent-resistant bacterium derived from the bacterium (Example 4) is an ostrich antibody-specific phenomenon which cannot be found in antibodies derived from other organism(s).

Example 5: Stability in the Gastrointestinal Tract of Ostrich Antibodies with *C. difficile* Components as Immunogen In the same manner as Example 1, mature female mice (C57BL) were orally administered with an aqueous solution in which ostrich IgY or chicken IgY against *C. difficile* toxin A made by using *C. difficile* toxin A as an immunogen was dissolved (5 mg antibody/mL) in a dose of 1 mg antibody/mouse (5 mice for each antibody).

After administration, excrements were collected from the anus every hour and excrements of 5 mice were collectively dissolved in PBS with 20 times the amount by weight of the excrements to be used for ELISA. 10-fold diluted solution of the antibodies orally administered to the mice was used as "antibody liquid" for ELISA.

The same experiment was conducted for antibodies with *C. difficile* toxin B as an immunogen. Specifically, in the same manner as Example 1, mature female mice (C57BL) were orally administered with an aqueous solution in which ostrich IgY or chicken IgY against *C. difficile* toxin B made by using *C. difficile* toxin B as an immunogen was dissolved (5 mg antibody/mL) in a dose of 1 mg antibody/mouse (5 mice for each antibody).

After administration, excrements were collected from the anus every hour and excrements of 5 mice were collectively dissolved in PBS with 20 times the amount by weight of the excrements to be used for ELISA. 10-fold diluted solution of the antibodies orally administered to the mice was used as "antibody liquid" for ELISA.

ELISA Measurement was Performed in the Same Manner as Example 1.

Figure 15:
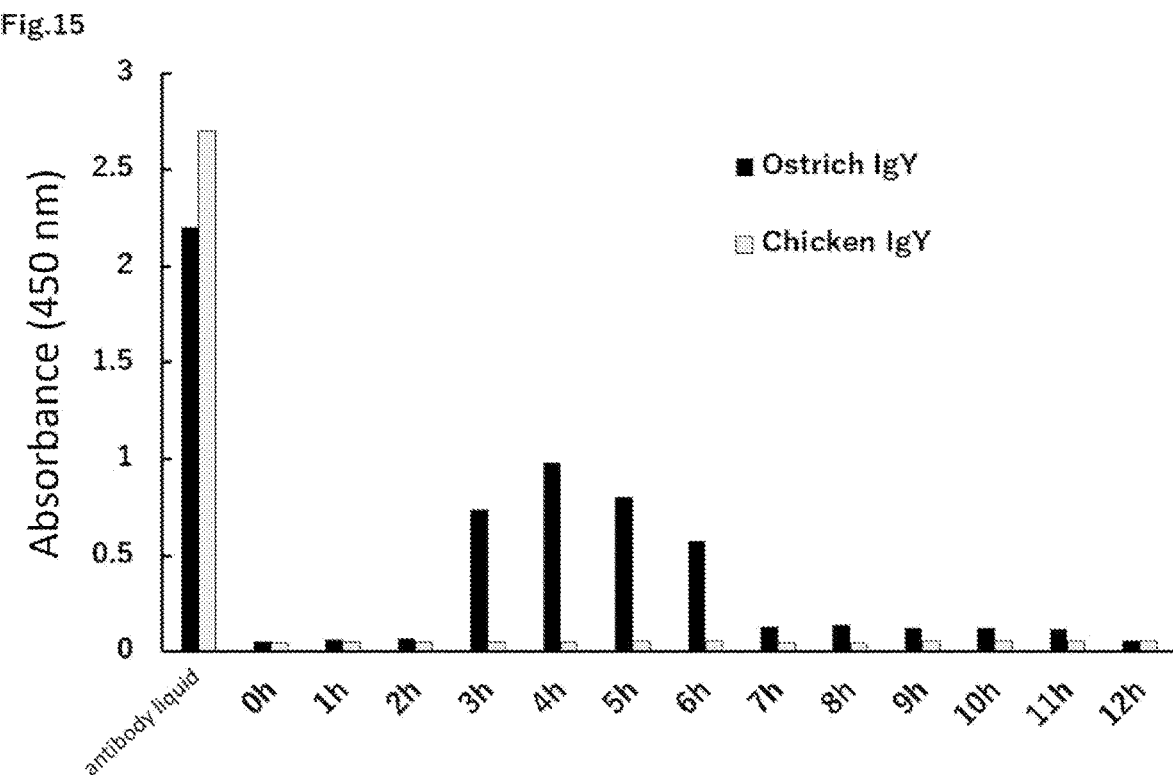
FIG. 15 shows the antibody activity in excrements from mice orally administered with an ostrich antibody and a chicken antibody of which immunogen is *C. difficile* toxin A over time.
Figure 16:
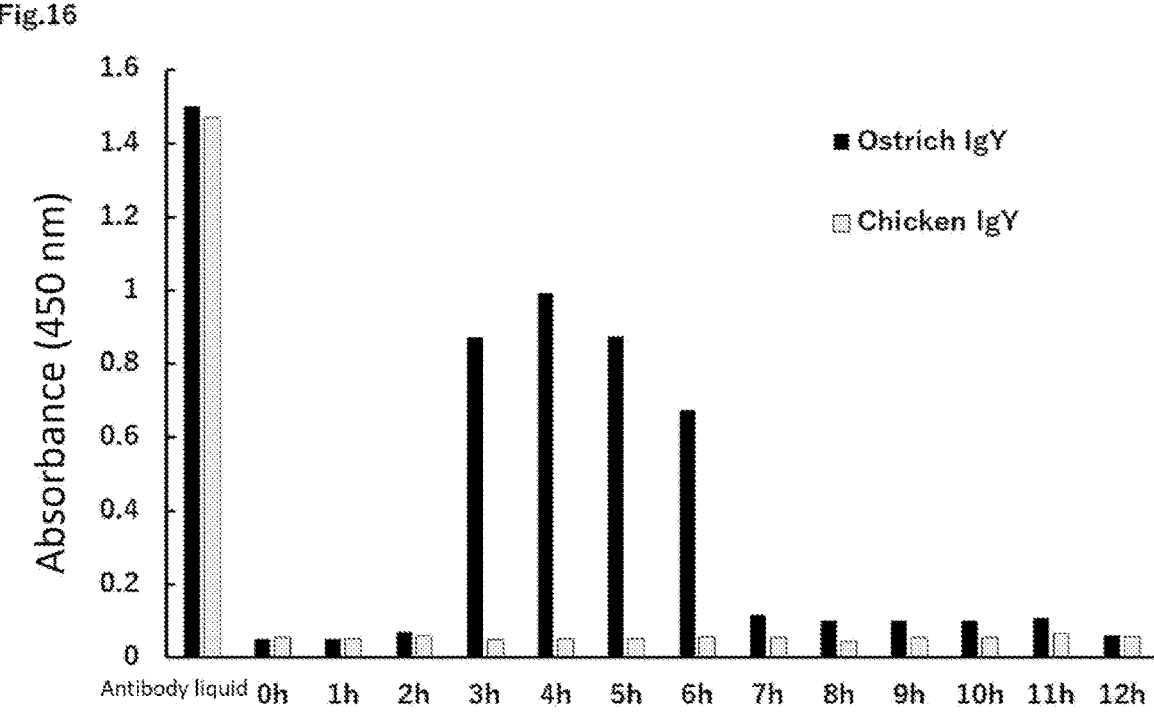
FIG. 16 shows the antibody activity in excrements from mice orally administered with an ostrich antibody and a chicken antibody of which immunogen is *C. difficile* toxin B over time.

The results of the antibodies with toxin A and toxin B as an immunogen are shown in FIG. 15 and FIG. 16, respectively. The result after 3 hours from administration revealed that both the anti-*C. difficile* toxin A antibodies and the anti-*C. difficile* toxin B antibodies obtained from ostriches retain binding activity with antigen in the excrements. Meanwhile, such activity was not observed in the chicken antibodies. This result indicates that the anti-*C. difficile* toxin A antibodies and the anti-*C. difficile* toxin B antibodies derived from ostriches are functional in the gastrointestinal tract despite the exposure to gastric acid and digestive enzymes after oral administration.

Example 6: Stability in the Gastrointestinal Tract of Ostrich Antibodies with Cholera Components as Immunogen Mature female mice (C57BL) were orally administered with an aqueous solution in which Ostrich IgY or Chicken IgY against cholera toxin made in the same manner as Example 3 was dissolved (5 mg antibody/mL) in a dose of 1 mg antibody/mouse (5 mice for each antibody).

After administration, excrements were collected from the anus every hour and excrements of 5 mice were collectively dissolved in PBS with 20 times the amount by weight of the excrements to be used for ELISA. 10-fold diluted solution of the antibodies orally administered to the mice was used as "antibody liquid" for ELISA.

ELISA Measurement was Performed in the Same Manner as Example 1.

Figure 17:
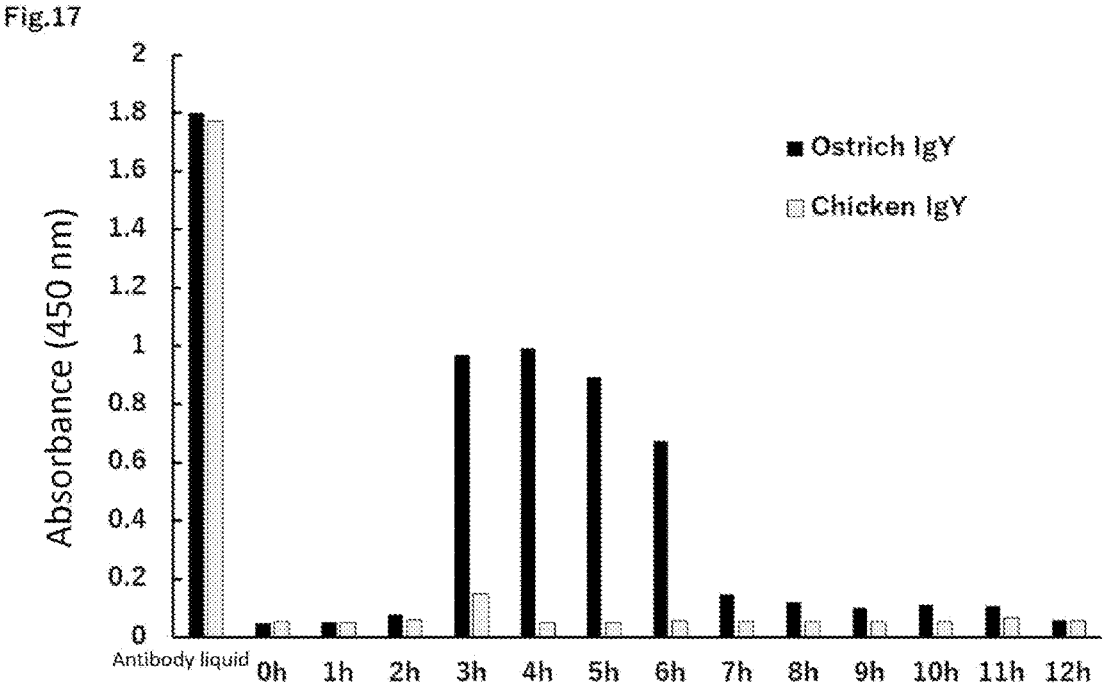
FIG. 17 shows the antibody activity in excrements from mice orally administered with an ostrich antibody and a chicken antibody of which immunogen is cholera toxin over time.

The result is shown in FIG. 17. The result after 3 hours from administration revealed that the anti-cholera toxin IgY obtained from ostriches retains binding activity with antigen in the excrements. Meanwhile, such activity was not observed in the Chicken IgY. This result indicates that the anti-cholera toxin IgY derived from ostriches is functional in the gastrointestinal tract despite the exposure to gastric acid and digestive enzymes after oral administration.

Example 7: Stability in Candies of Each Antibody

The stability of ostrich antibodies prepared as a candy was tested.

Each antibody was made in the following manner. In the same manner as Example 1, female ostriches or female chickens were immunized with *Vibrio cholerae* (homogenate or toxin), *Clostridium difficile* (homogenate or toxin), *Staphylococcus epidermidis* (homogenate or enterotoxin) as an immunogen and IgY was purified from eggs.

The homogenate was prepared in the following manner. Culture suspension of each bacterium was centrifuged and precipitated. Culture liquid was removed, phosphate buffer solution (pH 7) was added to float bacteria, and bacterial microbial cells were crushed with a homogenizer at 4° C. An ostrich was immunized with this homogenate.

In the same manner as Example 1, antibody titer was measured by ELISA, and the antibody liquid amount was adjusted so that each antibody titer would be 65536.

These antibodies were prepared as a candy in the following manner. Sugar and millet jelly were mixed and heated, each ostrich IgY (ELISA value 65536) or each chicken IgY (ELISA value 65536) was added to the mixture while dissolving it at 90° C., the mixture thereof was kneaded and cooled until the antibodies were uniformly dispersed over the whole mixture, and the mixture was formed so that each candy would be 3 g. One candy was dissolved in 10 mL of PBS, which was used as undiluted liquid for ELISA. As a control, pre-immune ostrich IgY (15 mg/mL) and pre-immune chicken IgY (15 mg/mL) were mixed so that each IgY would be 0.1 mL for each 3 g of candies.

Activity of the antibodies in the prepared candies was evaluated by ELISA. In this regard, ELISA was performed in the following manner. Solid phases of each antigen (2 μg) were formed separately at each well of a 96-well ELISA plate (4 hours at room temperature). Serially diluted solutions of dissolved solutions of candies mixed with each antibody were then dripped into each well and reacted for 1 hour at room temperature. After washing, HRP labeled-secondary antibodies for each antibody were reacted for 1 hour at room temperature. After thoroughly washing, a luminescent peroxidase assay kit (S-Bio SUMILON) was used to measure absorbance (450 nm) with a plate reader. The maximum dilution factor indicating 2 times the absorbance value or greater of pre-immune ostrich IgY or pre-immune chicken IgY are shown as the ELISA value. Since the base material of the candies would be an obstacle to ELISA measurement, samples used for ELISA measurement were diluted so as to contain the antibodies at a concentration which is half of the concentration upon preparation of candies.

As a result, ELISA values as shown in the following tables were measured.

TABLE 2

|  | *Vibrio cholerae* | |
| --- | --- | --- |
| Antibody | Microbial cell homogenate | Toxin |
| Ostrich IgY | 4094 | 8192 |
| Chicken IgY | 64 | 16 |

TABLE 3

|  | *Clostridium difficile* | | |
| --- | --- | --- | --- |
| Antibody | Microbial cell homogenate | Toxin A | Toxin B |
| Ostrich IgY | 8192 | 16384 | 8192 |
| Chicken IgY | 128 | 8 | 32 |

TABLE 4

| | Staphylococcus epidermidis | |
| Antibody | Microbial cell homogenate | Enterotoxin |
| --- | --- | --- |
| Ostrich IgY | 16 | 32 |
| Chicken IgY | 32 | 32 |

High activity was found in the ostrich IgY against cholera and *C. difficile* even when processed into candies, whereas the chicken IgY was mostly deactivated. Since the measurement ELISA value is calculated as 32768 when all antibodies maintain the activity, it can be calculated that regarding ostrich antibodies, for example, 12.5% of the anti-cholera microbial homogenate antibodies and 50% of the anti-*C. difficile* toxin A antibodies maintained the activity even after made into candies. Regarding *Staphylococcus epidermidis*, both the ostrich IgY and chicken IgY were deactivated.

These results revealed that the ostrich IgY can retain high antigen reactivity even when processed into candies, and that the stability of the ostrich antibodies can vary depending on the target antigen.

INDUSTRIAL APPLICABILITY

Pharmaceutical products and foods (such as candy) for treating (therapy and prevention) infectious diseases due to bacteria are provided by the present invention.

The invention claimed is:

1. A method of manufacturing ostrich antibodies, comprising immunizing mature female ostriches with a mixture solution comprising *Clostridium difficile* toxin A and toxin B, obtaining eggs from the immunized ostriches, and purifying egg yolk antibodies from the eggs, wherein the immunizing comprises priming the mature female ostriches with the mixture solution comprising *Clostridium difficile* toxin A and toxin B and boosting the ostriches with a mixture solution comprising *Clostridium difficile* toxin A and toxin B.

2. The method of claim 1, wherein the immunizing comprises priming the mature female ostriches with the mixture solution comprising *Clostridium difficile* toxin A and toxin B and boosting the ostriches with a mixture solution comprising *Clostridium difficile* toxin A and toxin B in week 2 and week 4 after the priming.

3. The method of claim 1, wherein the immunizing comprises priming the mature female ostriches with the mixture solution comprising *Clostridium difficile* toxin A and toxin B, and Freund's Complete Adjuvant and boosting the ostriches with a mixture solution comprising *Clostridium difficile* toxin A and toxin B, and Freund's Complete Adjuvant.

4. The method of claim 1, wherein the immunizing comprises priming the mature female ostriches with the mixture solution comprising 50 µg of *Clostridium difficile* toxin A, 50 µg of *Clostridium difficile* toxin B, and 0.2 mL of Freund's Complete Adjuvant and boosting the ostriches with a mixture solution comprising 50 µg of *Clostridium difficile* toxin A, 50 µg of *Clostridium difficile* toxin B, and 0.2 mL of Freund's Complete Adjuvant.

5. The method of claim 1, wherein the immunizing comprises priming the mature female ostriches with the mixture solution comprising 50 µg of *Clostridium difficile* toxin A, 50 µg of *Clostridium difficile* toxin B, and 0.2 mL of Freund's Complete Adjuvant and boosting the ostriches with a mixture solution comprising 50 µg of *Clostridium difficile* toxin A, 50 µg of *Clostridium difficile* toxin B, and 0.2 mL of Freund's Complete Adjuvant in week 2 and week 4 after the priming.

6. The method of claim 5, wherein the obtaining comprises obtaining eggs from the immunized ostriches in week 8 after the priming.

7. The method of claim 1, wherein the immunizing comprises inoculating the mixture solution into the muscle of the loin of the ostriches.

8. The method of claim 7, wherein the priming comprises inoculating the mixture solution into the muscle of the loin of the ostriches and the boosting comprises inoculating the mixture solution into the muscle of the loin of the ostriches.

9. A method of treating a gastrointestinal tract in a subject with an infectious disease of *Clostridium difficile,* comprising manufacturing ostrich antibodies according to claim 8, administering a therapeutically effective amount of the ostrich antibodies to the subject.

* * * * *